(12) United States Patent
Weiler

(10) Patent No.: US 8,533,877 B2
(45) Date of Patent: Sep. 17, 2013

(54) PATIENT TROLLEY

(75) Inventor: Herbert Weiler, Alling (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 13/007,353

(22) Filed: Jan. 14, 2011

(65) Prior Publication Data

US 2011/0173752 A1    Jul. 21, 2011

(30) Foreign Application Priority Data

Jan. 19, 2010  (DE) .......................... 10 2010 005 015

(51) Int. Cl.
*A47B 13/00*    (2006.01)

(52) U.S. Cl.
USPC ................................... 5/601; 5/620

(58) Field of Classification Search
USPC ............... 5/84.1, 510, 601, 86.1, 625, 626, 5/661
See application file for complete search history.

(56) References Cited

U.S. PATENT DOCUMENTS

| | | | | |
|---|---|---|---|---|
| 6,526,609 B2 * | 3/2003 | Wong | | 5/601 |
| 6,640,364 B1 * | 11/2003 | Josephson et al. | | 5/601 |
| 6,665,894 B2 * | 12/2003 | Moffa et al. | | 5/86.1 |
| 6,973,689 B2 * | 12/2005 | Lenting et al. | | 5/601 |
| 7,386,899 B2 * | 6/2008 | Smith | | 5/507.1 |
| 7,970,452 B2 * | 6/2011 | Piron et al. | | 600/411 |
| 2006/0048297 A1 * | 3/2006 | Mills | | 5/86.1 |
| 2007/0016003 A1 * | 1/2007 | Piron et al. | | 600/415 |
| 2007/0020070 A1 | 1/2007 | Venkatachalapathy | | |
| 2008/0263769 A1 * | 10/2008 | Newkirk et al. | | 5/503.1 |

FOREIGN PATENT DOCUMENTS

DE    10 2006 030 126 A1    1/2007
EP     0 630 637 A1    12/1994

OTHER PUBLICATIONS

German Office Action dated Apr. 4, 2011 for corresponding German Patent Application No. DE 10 2010 005 015.6-35 with English translation.

* cited by examiner

*Primary Examiner* — William Kelleher
*Assistant Examiner* — Richard G Davis
(74) *Attorney, Agent, or Firm* — Lempia Summerfield Katz LLC

(57) ABSTRACT

A trolley for transporting a patient includes a couch for the patient, an extendable and retractable component, and a coupling device on the extendable and retractable component for coupling the trolley to a medical apparatus. The couch and the extendable and retractable component are arranged such that extending or retracting the extendable and retractable component when the trolley is coupled to the medical apparatus (NMR) causes a relative movement of the couch with respect to the medical apparatus.

16 Claims, 2 Drawing Sheets

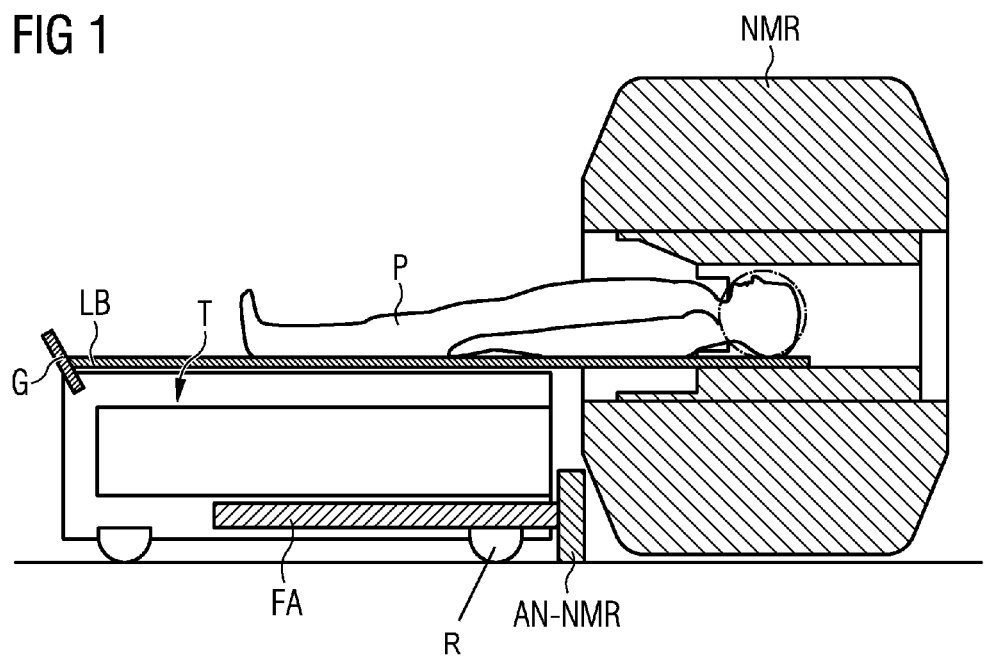

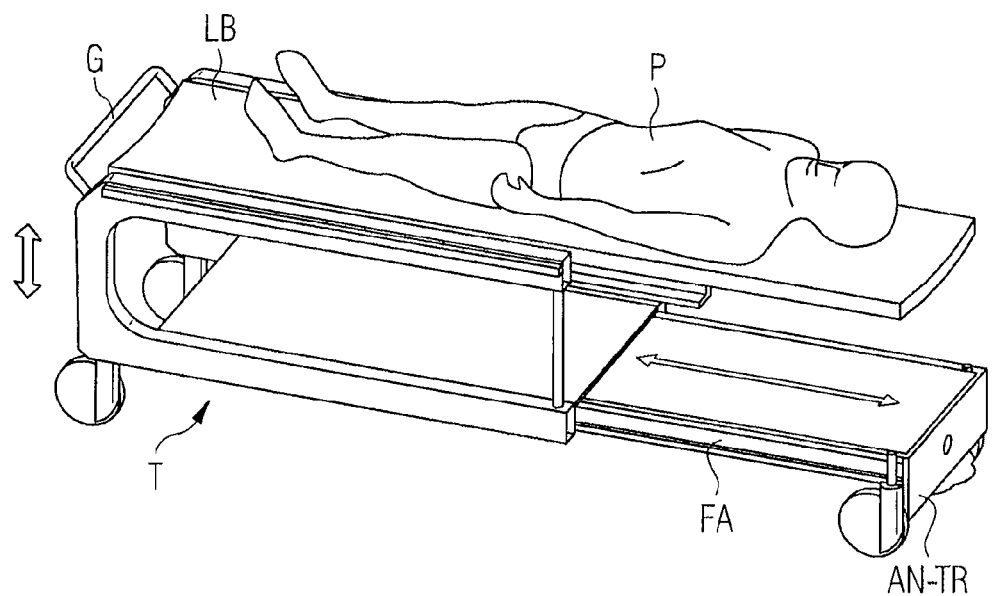
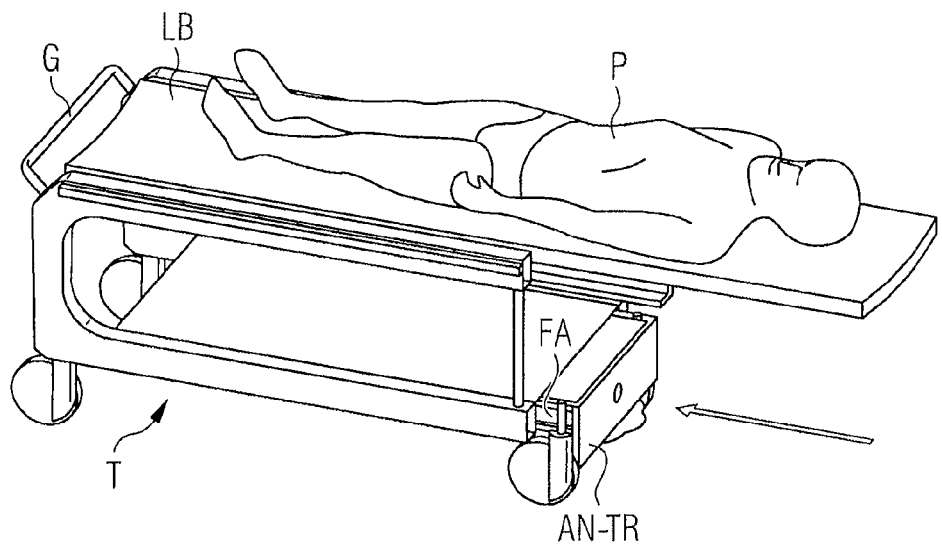

PATIENT TROLLEY

This application claims the benefit of DE 10 2010 005 015.6, filed Jan. 19, 2010.

BACKGROUND

The present embodiments relate to a trolley for transporting a patient.

In medical engineering, two-dimensional cross-sectional images (slices) or three-dimensional volume images of patients may be generated and analyzed using suitable tomographic methods. An example of such an imaging method for visualizing structures inside the body of a patient is magnetic resonance tomography (MRT); MRT is based on the physical phenomenon of nuclear magnetic resonance (NMR) and has been employed with success for over 15 years in medicine and in biophysics. With MRT, images that permit an excellent appraisal of the organs and a multiplicity of organ changes may be generated. Another tomographic method is computed tomography (CT). In CT, the patient is irradiated with x-rays from different viewing angles, and an image of the patient is reconstructed from these projections.

In an imaging medical diagnostic apparatus, an NMR or CT scanner for example, a displaceable patient positioning device of the apparatus for an examination subject (e.g., a patient) is used for supporting the examination subject thereon and introducing the subject into an imaging volume of the apparatus. The patient positioning device may be stationary and mechanically coupled to the apparatus.

SUMMARY AND DESCRIPTION

The present embodiments may obviate one or more of the drawbacks or limitations in the related art. For example, in one embodiment, an improved medical apparatus for positioning a patient during an examination may be provided.

The trolley for transporting a patient of the present embodiments has a couch for the patient, a component that is extendable and retractable, and a coupling device on the extendable and retractable component for coupling the trolley to a medical apparatus. The couch and the extendable and retractable component are arranged, such that extending or retracting the extendable and retractable component when the trolley is coupled to the medical apparatus causes a relative movement of the couch with respect to the medical apparatus.

The trolley is used to transport the patient. This is achieved in that the patient lies or sits on the couch, and the trolley is moved.

The extendable and retractable component may be implemented, for example, using a guide including one or more guide rails, on which the component may be moved back and forth. The arrangement of the extendable and retractable component at one end of the guide corresponds to the extended position of the component, and the arrangement of the extendable and retractable component at the other end of the guide corresponds to the retracted position of the component.

The coupling device is located on the extendable and retractable component. This enables the trolley to be connected to the medical apparatus. For connecting the trolley to the medial apparatus, the coupling device cooperatively interacts with a corresponding coupling device of the medical apparatus. As a result of the coupling, the trolley is docked or secured to the medical apparatus; this attachment may be canceled again by releasing the coupling.

The medical apparatus may be an examination or treatment apparatus such as, for example, an NMR scanner or a CT scanner.

The trolley may be used as a patient positioning device during an examination or treatment using the medical apparatus. In order to introduce the patient into the medical apparatus, the extendable and retractable component is retracted or extended with the trolley in the coupled state. This causes the couch carrying the patient to move relative to the medical apparatus. During the examination or treatment using the medical apparatus, the patient may remain on the couch.

The extendable and retractable component may be retracted and/or extended without use of an electromotive drive. For example, a handle may be provided on the trolley to enable the trolley to be pulled or pushed, thereby effecting the retraction or extension movement.

It is advantageous if the extendable and retractable component is extendable and retractable in the longitudinal direction of the couch. The longitudinal direction or axis of the couch corresponds to the longitudinal axis of the patient disposed on the couch. The relative movement of the couch with respect to the medical apparatus takes place along the longitudinal axis of the couch.

In one embodiment, the trolley includes a frame, on which the couch and the extendable and retractable component are disposed, the extendable and retractable component being located underneath the couch. The extendable and retractable component may be arranged on a lower part of the trolley.

In one embodiment, the trolley has a locking device that, in the locked state, prevents the extension and retraction of the extendable and retractable component. The locking device has a locked and a released state, where in the locked state, as opposed to the released state, the extendable and retractable component may not be extended or retracted. The locking device may be arranged in the medical apparatus or may correspond to a cooperative interaction between components of the trolley and of the medical apparatus.

It is advantageous if a mechanism is provided to allow the automatic release of the locking device when the trolley is coupled to the medical apparatus. The coupling action causes a locking state to be released so that the extendable and retractable component may be extended or retracted. The release of the locking state is effected automatically (e.g., without the need for an operator to do anything for that purpose beyond the coupling).

In one embodiment, the trolley has a mechanism for automatically locking the locking device when a fully retracted position of the extendable and retractable component is reached with the trolley coupled to the medical apparatus. The fully retracted position of the extendable and retractable component may correspond to the positioning of the patient at a desired position inside the medical apparatus, such that the desired position is fixed by the locking mechanism.

The locking device may be released by an operator using a release device provided on the trolley. This enables a locking state (e.g., previously set automatically) to be canceled by human actuation of the release device.

In one embodiment, the trolley includes a mechanism for automatically locking the locking device when the trolley is decoupled from the medical apparatus. When the trolley is removed from the medical apparatus, the extendable and retractable component may no longer be extended or retracted. This stabilizes the trolley during the transportation of the patient.

For locomotion purposes, the trolley is fitted with wheels. It is advantageous if some of the wheels are connected to the extendable and retractable component, such that the wheels are moved when the extendable and retractable component is extended or retracted.

BRIEF DESCRIPTION OF THE DRAWINGS

FIG. 1 shows one embodiment of a patient trolley docked to a magnetic resonance scanner;
FIG. 2 shows one embodiment of a patient trolley in a parked position; and
FIG. 3 shows one embodiment of a patient trolley in a docking position.

DETAILED DESCRIPTION OF THE DRAWINGS

Patient trolleys are used for transporting a patient in a hospital or similar facility. If, for example, a magnetic resonance or computed tomography scan of a patient is to be performed, the patient is placed onto the patient trolley, and the patient trolley is wheeled to the medical apparatus. The NMR or CT scanner may have a patient positioning device that is permanently installed on the apparatus and, onto which the patient is lifted from the patient trolley. During the measurement, the patient is disposed on the patient positioning device and subsequently is transferred back to the patient trolley and removed with the patient trolley from the medical apparatus. The movements from the patient trolley to the patient positioning device and from the patient positioning device to the patient trolley may be disadvantageous for the patient in certain circumstances. If the patient is injured, for example, transfers of this kind are painful or even dangerous.

FIG. 1 shows one embodiment of a patient trolley. The patient trolley T includes a couch board LB, on which the patient P lies. The couch board LB is fixedly attached to the patient trolley T. The trolley T, which has wheels R, may be pushed by a handle G. In the illustration of FIG. 1, the patient trolley T is docked to a magnetic resonance scanner NMR. For docking, the magnetic resonance scanner NMR includes a docking device AN-NMR. The docking device AN-NMR cooperatively interacts with the patient trolley T, such that the patient trolley T may be secured and locked to the docking device AN-NMR.

On a lower part of the patient trolley T, the patient trolley T includes an extendable component in the form of a guide slide-out FA. FIG. 2 shows the patient trolley T with the guide slide-out FA extended, whereas in FIG. 3, the patient trolley T is shown with the guide slide-out FA retracted. Two front wheels R of the patient trolley T are located at a front end of the guide slide-out FA. The two front wheels R are moved when the guide slide-out FA is pushed in or withdrawn.

The extended position of the guide slide-out FA according to FIG. 2 is used for transporting the patient P on the patient trolley T. In the extended position, owing to the location of the two front wheels R, the patient trolley T may not overturn even when carrying heavy patients P or if someone leans on a head end of the couch board LB.

When the guide slide-out FA is in the extended position, the guide slide-out FA is locked. The locking may be realized using a suitable bolt. In other words, without unlocking, the guide slide-out FA may not be pushed in and thus moved into the position shown in FIG. 3.

The locking prevents the guide slide-out FA from being unintentionally pushed in, which would increase the risk of the patient trolley T overturning.

With the guide slide-out FA in the extended position according to FIG. 2, the patient trolley T is maneuvered to the magnetic resonance scanner NMR by pushing on the handle G, for example. A front part of the guide slide-out FA includes a docking device AN-TR that cooperatively interacts with the docking device AN-NMR of the magnetic resonance scanner NMR. The docking device AN-NMR may be included in the scope of delivery of the trolley T and is attached to the magnetic resonance scanner NMR using a screwed connection.

The engagement of the two docking devices AN-TR and AN-NMR causes the guide slide-out FA to be unlocked. This may be effected using, for example, a projection on the docking device AN-TR. In other words, as soon as the patient trolley T is coupled to the magnetic resonance scanner NMR, the guide slide-out FA may be pushed in.

The docking device AN-NMR of the magnetic resonance scanner NMR is configured such that the patient trolley T does not need to be precisely brought into contact with the docking device AN-NMR at a specific angle in order to effect a docking. It is advantageous, for example, if the docking device AN-NMR has a tolerance range of 45° on both sides, such that the patient trolley T may be maneuvered toward the magnetic resonance scanner NMR at 45° on either side and docked.

After docking, the guide slide-out FA is retracted by pushing on the handle G in the direction of the magnetic resonance scanner NMR and thus brought into the position shown in FIGS. 1 and 3. This automatically causes the couch board LB supporting the patient P to be inserted into the magnetic resonance scanner NMR. When the guide slide-out FA is in the fully retracted state, the patient P has reached a position for the measurement inside the magnetic resonance scanner NMR. For this purpose, the length of the guide slide-out FA (e.g., the distance, by which the guide slide-out FA is displaced from the extended position into the retracted position) is adjusted to match the dimensions of the magnetic resonance scanner NMR.

A motor for delivering a horizontal drive, as may be provided for permanently installed patient couches of medical apparatuses, may not be included, since the patient trolley T may be pushed using the handle G. An advantage with this arrangement is that neither a connection to a power source nor a battery is used in order to convey the patient P into the magnetic resonance scanner NMR.

Reaching the fully retracted position of the guide slide-out FA causes the the guide slide-out FA to be locked once again. In other words, in the position shown in FIGS. 1 and 3, the guide slide-out FA may not be unintentionally extended. This prevents the couch board LB from moving during the measurement and consequently, the patient P being moved out of the measurement field. Following completion of the data acquisition, the guide slide-out FA may be manually unlocked. For manually unlocking, a lever or similar device is provided at a suitable position on the patient trolley T or on the docking device AN-NMR of the magnetic resonance scanner NMR. The guide slide-out FA is unlocked using a hand- or foot-controlled operation. Alternatively, measurement software may send a control command that initiates an automatic unlocking of the guide slide-out FA following completion of the data acquisition.

Using the patient trolley T of the present embodiments, a patient couch that is permanently attached to the magnetic resonance scanner NMR may no longer be needed or used. The patient trolley T may accordingly be a movable patient couch or patient positioning device. By virtue of the patient trolley T, the patient P acquires mobility and may be transported from any location (e.g., from his or her hospital room or from a specific treatment room, to the magnetic resonance scanner NMR). Because no transfer takes place from the patient trolley T to a patient positioning device of the magnetic resonance scanner NMR, this form of handling is very patient-friendly.

An NMR head scanner is shown in FIG. 1. The patient trolley T may, however, also be used for other imaging examination equipment (e.g., for other types of NMR scanners or for CT (computed tomography) scanners). For this purpose, the couch board LB may also be displaceable beyond the displacement distance of the guide slide-out FA. In one embodiment, a motor-powered drive may also be provided on the patient trolley T, the drive being operable to retract the couch board LB to different depths into the medical apparatus. The horizontal electromotive drive is used when the position shown in FIG. 1 is reached as a result of full insertion of the guide slide-out FA.

In one embodiment, the patient trolley T includes a height adjustment capability. This is of advantage, for example, when the patient trolley T is to be used for different medical apparatuses. A height adjustability of this kind may be achieved using, for example, adjusting screws on the wheels of the patient trolley T.

The patient trolley T allows a very precise positioning of the patient P in the measurement field. The mechanics of the docking mechanism and guide rails of the guide slide-out FA are precisely adjustable. The patient is therefore brought into the desired position corresponding to the measurement field by complete retraction of the guide slide-out FA. The desired position is reproducible, which is advantageous for any further measurement that may be necessary.

On sides of the patient trolley T, the patient trolley T may have standard profile rails that may accommodate typical hospital accessories such as, for example, infusion poles.

Suitable dimensions for the patient trolley T are, for example, 2.4 meters for the couch board LB, 1.5 meters for the lower part of the patient trolley T when the guide slide-out FA is fully inserted, and 0.9 meters for the extension capability of the guide slide-out FA.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A trolley for transporting a patient, the trolley comprising:
   a couch for the patient;
   an extendable and retractable component;
   a coupling device disposed on an end of the extendable and retractable component for coupling the trolley to a medical apparatus;
   a frame on which the couch and the extendable and retractable component are located, the frame comprising a top and a bottom, a distance between the bottom of the frame and a surface supporting the trolley being less than a distance between the top of the frame and the surface supporting the trolley, the extendable and retractable component being located underneath the couch;
   a locking device operable to prevent the extendable and retractable component from being extended and retracted; and
   a mechanism operable to automatically release the locking device when the trolley is coupled to the medical apparatus via the coupling device disposed on the end of the extendable and retractable component,
   wherein the couch and the extendable and retractable component are arranged, such that retracting the extendable and retractable component when the trolley is coupled to the medical apparatus causes the couch to move into, above, or below the medical apparatus, and
   wherein the extendable and retractable component is disposed on the frame at a position closer to the bottom of the frame than the top of the frame.

2. The trolley as claimed in claim 1, wherein the extendable and retractable component is extendable and retractable in the longitudinal direction of the couch.

3. The trolley as claimed in claim 1, further comprising a mechanism for automatically locking the locking device when a fully retracted position of the extendable and retractable component is reached with the trolley coupled to the medical apparatus.

4. The trolley as claimed in claim 1, further comprising a release device, the locking device being operable to be released by an operator using the release device.

5. The trolley as claimed in claim 3, further comprising a mechanism for automatically locking the locking device when the trolley is decoupled from the medical apparatus.

6. The trolley as claimed in claim 1, further comprising wheels, wherein some of the wheels are connected to the extendable and retractable component, such that the wheels are moved when the extendable and retractable component is extended or retracted.

7. A medical apparatus comprising:
   a trolley for transporting a patient, the trolley comprising:
      a couch for the patient;
      an extendable and retractable component;
      a coupling device disposed on an end of the extendable and retractable component for coupling the trolley to the medical apparatus;
      a frame on which the couch and the extendable and retractable component are located, the frame comprising a top and a bottom, a distance between the bottom of the frame and a surface supporting the trolley being less than a distance between the top of the frame and the surface supporting the trolley, the extendable and retractable component being located underneath the couch;
      a locking device operable to prevent the extendable and retractable component from being extended and retracted; and
      a mechanism operable to automatically release the locking device when the trolley is coupled to the medical apparatus via the coupling device disposed on the end of the extendable and retractable component,
   wherein the couch and the extendable and retractable component are arranged, such that retracting the extendable and retractable component when the trolley is coupled to the medical apparatus causes the couch to move into, above, or below the medical apparatus, and
   wherein the extendable and retractable component is disposed on the frame at a position closer to the bottom of the frame than the top of the frame.

8. The medical apparatus as claimed in claim 7, wherein the trolley is coupled to the medical apparatus.

9. The trolley as claimed in claim 2, further comprising a mechanism for automatically locking the locking device when a fully retracted position of the extendable and retractable component is reached with the trolley coupled to the medical apparatus.

10. The trolley as claimed in claim 2, further comprising a release device, the locking device being operable to be released by an operator using the release device.

11. The trolley as claimed in claim 3, further comprising a release device, the locking device being operable to be released by an operator using the release device.

12. The trolley as claimed in claim 1, further comprising a mechanism for automatically locking the locking device when the trolley is decoupled from the medical apparatus.

13. The trolley as claimed in claim 2, further comprising a mechanism for automatically locking the locking device when the trolley is decoupled from the medical apparatus.

14. The trolley as claimed in claim 4, further comprising a mechanism for automatically locking the locking device when the trolley is decoupled from the medical apparatus.

15. The trolley as claimed in claim 2, further comprising wheels, wherein some of the wheels are connected to the extendable and retractable component, such that the wheels are moved when the extendable and retractable component is extended or retracted.

16. The trolley as claimed in claim 3, further comprising wheels, wherein some of the wheels are connected to the extendable and retractable component, such that the wheels are moved when the extendable and retractable component is extended or retracted.

* * * * *